(12) United States Patent
McDonald et al.

(10) Patent No.: US 10,080,629 B2
(45) Date of Patent: Sep. 25, 2018

(54) DENTAL RESTORATIVE DEVICE AND METHOD OF USING THE SAME

(71) Applicant: Rhondium IP Limited, Katikati (NZ)

(72) Inventors: Simon P. McDonald, Katikati (NZ); Alejandro Aubone, Katikati (NZ)

(73) Assignee: RHONDIUM IP LIMITED, Katikati (NZ)

( * ) Notice: Subject to any disclaimer, the term of this patent is extended or adjusted under 35 U.S.C. 154(b) by 0 days.

(21) Appl. No.: 15/110,323

(22) PCT Filed: Jan. 8, 2015

(86) PCT No.: PCT/US2015/010579
§ 371 (c)(1),
(2) Date: Jul. 7, 2016

(87) PCT Pub. No.: WO2015/105945
PCT Pub. Date: Jul. 16, 2015

(65) Prior Publication Data
US 2016/0324604 A1 Nov. 10, 2016

(30) Foreign Application Priority Data

Jan. 9, 2014 (NZ) .......................................... 619788
Apr. 2, 2014 (NZ) .......................................... 623337
(Continued)

(51) Int. Cl.
*A61C 5/10* (2006.01)
*A61C 13/107* (2006.01)
(Continued)

(52) U.S. Cl.
CPC ............ *A61C 13/0001* (2013.01); *A61C 5/73* (2017.02); *A61C 5/77* (2017.02); *A61C 5/88* (2017.02);
(Continued)

(58) Field of Classification Search
CPC ... A61C 13/0001; A61C 13/087; A61C 13/09; A61C 13/083; A61C 5/88; A61C 5/77;
(Continued)

(56) References Cited

U.S. PATENT DOCUMENTS 2,219,058 A 10/1940 Streim
5,186,626 A 2/1993 Tanaka
(Continued)

FOREIGN PATENT DOCUMENTS

CN 2078612 U 6/1991
CN 2131485 Y 5/1993
(Continued)

OTHER PUBLICATIONS

European Patent Office, International Search Report, PCT/US2015/10579, dated Jun. 4, 2015.
(Continued)

*Primary Examiner* — Matthew Nelson
(74) *Attorney, Agent, or Firm* — IpHorgan Ltd.

(57) ABSTRACT

A dental restorative device is shown as comprising a first cured or hardened layer in the form of an occlusal surface of the tooth being restored and a second uncured dental composite layer joined to the first layer enabling a dental professional to perform direct dental restoration procedures with results replicating indirect direct dental restoration procedures. A system comprising the multi-layered dental restorative device and packaging provides for sufficient support and protection of the uncured second layer and facilitates positioning and finishing of the dental restorative device by cooling the uncured portions to a rigid state while in the packaging, positioning the dental restorative device, and modifying the second layer to fit, curing the second layer and permanently placing the fully cured and hardened dental crown on the tooth being restored.

10 Claims, 11 Drawing Sheets

(30) Foreign Application Priority Data

Jun. 9, 2014 (NZ) .......................................... 626009
Aug. 20, 2014 (NZ) .......................................... 629085

(51) Int. Cl.

| | | |
|---|---|---|
| A61C 13/083 | (2006.01) | |
| A61C 13/087 | (2006.01) | |
| A61C 13/09 | (2006.01) | |
| A61K 6/02 | (2006.01) | |
| A61C 19/02 | (2006.01) | |
| A61C 5/77 | (2017.01) | |
| A61C 5/88 | (2017.01) | |
| A61C 13/00 | (2006.01) | |
| A61C 5/73 | (2017.01) | |
| A61C 19/04 | (2006.01) | |
| A61C 13/15 | (2006.01) | |

(52) U.S. Cl.
CPC ........ *A61C 13/0022* (2013.01); *A61C 13/083* (2013.01); *A61C 13/087* (2013.01); *A61C 13/09* (2013.01); *A61C 19/02* (2013.01); *A61K 6/0205* (2013.01); *A61C 19/003* (2013.01); *A61C 19/04* (2013.01); *A61C 2202/01* (2013.01)

(58) Field of Classification Search
CPC ....... A61C 19/003; A61C 19/02; A61C 19/04; A61C 2202/01; A61K 6/0205
USPC .............................. 433/215, 223, 218, 202.1
See application file for complete search history.

(56) References Cited

U.S. PATENT DOCUMENTS

| | | | | |
|---|---|---|---|---|
| 5,192,207 A | * | 3/1993 | Rosellini ................. | A61C 5/00 264/19 |
| 5,839,900 A | | 11/1998 | Billet | |
| 6,068,481 A | | 5/2000 | Worthington | |
| 6,726,472 B2 | | 4/2004 | Kuhn | |
| 6,935,862 B2 | | 8/2005 | Harlan | |
| 7,163,395 B2 | | 1/2007 | Chu | |
| 7,726,970 B2 | * | 6/2010 | Worthington ...... | A61C 13/0001 433/183 |
| 7,816,423 B2 | | 10/2010 | Karim | |
| 2003/0039943 A1 | * | 2/2003 | Worthington ...... | A61C 13/0001 433/218 |
| 2003/0170593 A1 | * | 9/2003 | Dorfman .................. | A61C 5/00 433/226 |
| 2003/0203339 A1 | * | 10/2003 | Chilibeck ................ | A61C 5/70 433/218 |
| 2004/0106085 A1 | * | 6/2004 | Vallittu .................... | A61K 6/08 433/167 |
| 2008/0096166 A1 | | 4/2008 | Morris | |
| 2009/0258965 A1 | | 10/2009 | Lassila | |
| 2010/0021868 A1 | * | 1/2010 | Kvitrud .................... | A61C 5/00 433/223 |
| 2012/0100501 A1 | * | 4/2012 | Huynh ............... | A61C 13/0001 433/172 |

FOREIGN PATENT DOCUMENTS

| | | |
|---|---|---|
| CN | 2149186 Y | 12/1993 |
| CN | 101489518 B | 4/2013 |
| EP | 0087022 A1 | 8/1983 |
| EP | 0585231 B1 | 3/1994 |
| EP | 1078607 A3 | 2/2003 |
| EP | 1854427 A1 | 11/2007 |
| EP | 2050415 A1 | 4/2009 |

OTHER PUBLICATIONS

European Patent Office, International Preliminary Report on Patentability, PCT/US2015/10579, dated Dec. 21, 2015.
European Patent Office, International Preliminary Report on Patentability, PCT/US2015/10579, dated Jun. 16, 2016.
International Preliminary Examining Authority, International Preliminary Report on Patentability, dated Dec. 9, 2016.

* cited by examiner

DENTAL RESTORATIVE DEVICE AND METHOD OF USING THE SAME

CROSS-REFERENCE TO RELATED APPLICATIONS

This application is a National Phase application of International Application No. PCT/US2015/010579, filed on Jan. 8, 2015, which in turn claims priority to New Zealand Provisional Patent Application Nos.: 623337, filed on Apr. 2, 2014; 619788, filed Jan. 9, 2014; 629085, filed Aug. 20, 2014; and 626009, filed on Jun. 9, 2014, the contents of which are all hereby incorporated by reference.

FIELD OF THE INVENTION

This invention relates generally to the field of restorative dentistry and more specifically to the method of restoring an affected tooth to undamaged state replicating a natural, undamaged tooth using a dental restorative device comprising a cured and/or heat-treated layer joined to a user configurable uncured sub-layer allowing for in situ customization of the dental restorative device.

BACKGROUND OF THE INVENTION

Restoration of a tooth can either be direct or indirect. Direct restoration involves the reconstruction of a large volume of lost tooth structure using a dental restorative material. Indirect restoration involves the placement of an onlay or crown manufactured outside the mouth from a virtual or physical model of the affected tooth. Traditionally, metal crowns have been made using gold and stainless steel. Currently, ceramic and composite crowns are also produced.

Tooth restoration using a crown is offered when the affected tooth is severely damaged, but requires the patient to visit the dentist at least twice. During the first visit, the dentist takes an impression of the missing or damaged tooth and sends it to a dental lab where the lab prepares a custom crown. The custom crown is fitted by the dentist during the patient's second visit. This procedure is both expensive and time consuming.

An alternate procedure offered is the complex MODBL (Mesial, Occlusal, Distal, Buccal, Lingual) direct restoration. This procedure is less expensive than a custom crown restoration and only requires one visit to the dentist. The procedure requires the missing and/or damaged portion of the tooth to be reconstructed with a dental restorative material such as dental composite, amalgam, gold foil or glass ionomer cements. In a majority of the cases, a complex composite restoration is not a long-term solution and will eventually require the patient to revisit the dentist for repair or replacement.

Currently, dentists are unable to offer a procedure to patients that is less expensive than a custom crown but stronger than a complex composite restoration. The dental restorative device described herein provides a solution to overcome the current drawback and other drawbacks of current devices and methods of restoration not expressly referred to herein.

SUMMARY OF THE INVENTION

In one aspect of the present invention, a dental restorative device for use in a restoration of an affected tooth requiring restoration from a damaged state to a restored state replicating a natural, undamaged tooth comprises a first layer composed of a first dental restoration material and formed into a first end-use configuration, and a second layer fixed to the first layer and composed of a first uncured dental composite material in a second end-use configuration. The first dental restoration material composing the first layer is a cured dental composite material or is a hardened dental ceramic and the second layer is a user configurable, uncured sub-layer enabling in situ customization of the dental restorative device. The first end-use configuration of the first layer replicates an occlusal surface of the natural, undamaged tooth and the second end-use configuration of the second layer forms a plurality of sidewalls replicating a buccal, lingual, mesial and distal sidewall of the natural, undamaged tooth. The first layer may also be described as a cured anatomical occlusal layer or a heat-treated anatomical occlusal layer. The dental restorative device further comprises a handle integrally formed with the first or second layer.

In another aspect the present invention, a method of restoring an affected tooth of a patient requiring restoration from a damaged state to a restored state replicating a natural, undamaged tooth, the method comprises the steps of:
  a) providing a dental restorative device comprising a first layer composed of a first dental restoration material prepared and formed into a first end-use configuration and a second layer joined to the first layer and composed of a user configurable uncured dental composite material in a second end-use configuration;
  b) cooling the second layer composed of the uncured dental composite material to a rigid form;
  c) positioning the dental restorative device with the cooled, rigid and uncured second layer onto the affected tooth with a prepared restoration site and allowing the cooled, rigid and uncured second layer to warm;
  d) configuring the warmed second layer and adjusting the dental restorative device to the bite registration of the patient;
  e) removing the dental restorative device from the restoration site and curing the second layer; and
  f) re-positioning the dental restorative device with the cured second layer and permanently joining the dental restorative device to the affected tooth at the restoration site.

The method may further comprise the step of storing the dental restorative device in packaging comprising an outer casing and an inner form, where the outer casing comprising a lid and a bottom and the inner form supporting the uncured, second layer of the dental restorative device in the second end-use configuration. The inner form is removed from the outer casing prior to the cooling step and the dental restorative device with the cooled, rigid second layer is removed from the inner form after the cooling step.

A selector key may be used to confirm a mesial-distal measurement of the restoration site and select the dental restorative device having a size corresponding to the mesial-distal measurement of the restoration site. A replica restoration of the dental restorative device is positioned in the prepared restoration site to test and confirm the positioning of the dental restoration device in relation to a first and second adjacent tooth and a first opposing tooth.

The first dental restoration material composing the first layer is a cured dental composite material or a hardened dental ceramic and the first end-use configuration of the first layer replicates an occlusal surface of the natural, undamaged tooth. The second end-use configuration of the second layer forms a plurality of sidewalls replicating a buccal, lingual, proximal and distal sidewall of the natural, undamaged tooth.

In a third aspect of the invention a dental restorative device and packaging system for storing, preparing and dispensing a dental restorative device for use in a restoration of an affected tooth requiring restoration from a damaged state to a restored state replicating a naturel, undamaged tooth, the dental restorative device and packaging system comprises a dental restorative device comprising a first layer composed of a first dental restoration material prepared and formed into a first end-use configuration and a second layer fixed to the first layer and composed of an uncured dental composite material in a second, end-use configuration; and packaging comprising an outer casing and an inner form, the outer casing comprising a lid and a bottom mechanically locked together, and the inner form adhered to the bottom and formed to store and support the uncured, second layer of the dental restorative device in the second end-use configuration. The inner form comprises a chamber for receiving the dental restorative device, the chamber composed of a material with a high thermal conductivity rating to facilitate cooling of the dental restorative device stored therein and sits on a platform portion of the bottom of the outer casing and the lid comprises a chamber with a first depth sufficient to receive the inner form chamber. The outer casing and inner form are composed of a light-transmission inhibiting material. The mechanical locking together of the lid and bottom also inhibits ambient light transmission into the chamber in the lid. The mechanical locking may be in the form of an annular snap-fit from corresponding ridges on the lid and bottom of the outer casing.

The first dental restoration material composing the first layer is a cured dental composite material or a hardened dental ceramic and the first end-use configuration of the first layer is an anatomical occlusal surface replicating an occlusal of the natural, undamaged tooth. The second end-use configuration of the second layer forms a plurality of sidewalls replicating a buccal, lingual, mesial and distal sidewall of the natural, undamaged tooth and is a user configured, uncured sub-layer enabling in situ customization of the dental restorative device.

In a fourth aspect of the invention a kit for use in restoration of an affected tooth requiring restoration from a damaged state to a restored, undamaged state replicating a natural, undamaged tooth, the kit comprises: a) dental restorative devices in a plurality of sizes, each comprising a first layer composed of a first dental restoration material prepared and formed into a first end-use configuration and a second layer fixed to the first layer and composed of an uncured dental composite material in a second, end-use configuration enabling customized shaping and finishing of the second layer; b) packaging comprising an outer casing and an inner form, the outer casing comprising a lid and a bottom each with corresponding grooves to mechanically join and lock the top to the bottom, and the inner form adhered to the bottom and formed to support the uncured, second layer of the dental restorative device in the second end-use configuration; and c) a selector key corresponding to the plurality of sizes of dental restorative devices in the kit. The selector key comprises a first edge and a second, stepped edge opposing the first edge and forming a plurality of widths of varying dimension between the first and second edges and each of the varying dimensions corresponds to a size of the plurality of dental restorative devices in the kit. The kit may further comprise a carving tool for shaping the second layer and removing uncured dental composite material during preparation of the dental restorative device, and a separating agent to be applied to the affected tooth and adjacent dentition during preparation and installation of the dental restorative device.

DETAILED DESCRIPTION OF THE DRAWINGS

The present inventive dental restorative device is a "hybrid" crown made of two main parts, namely, a first cured and/or heat-treated anatomical occlusal layer and a second uncured sub-layer with a handle to ease in grasping and maneuvering the dental crown. FIGS. 1-8 show various embodiments of the "one-visit" dental restorative device 10 of the present invention and its corresponding packaging. Like or identical elements in each figure will be identified with the same reference number whenever possible. The dental restorative device of the present invention significantly decreases the time taken by a dental professional to restore a damaged and/or missing native tooth and also eliminates guesswork by the dental professional regarding the shade and amount of composite required.

Figure 1:
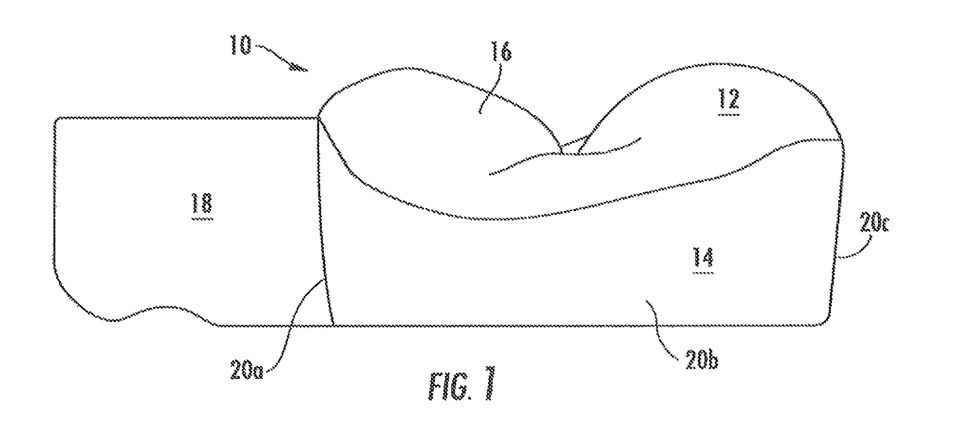
FIG. 1 is a side elevation view of an embodiment of the present inventive dental restorative device.
Figure 2:
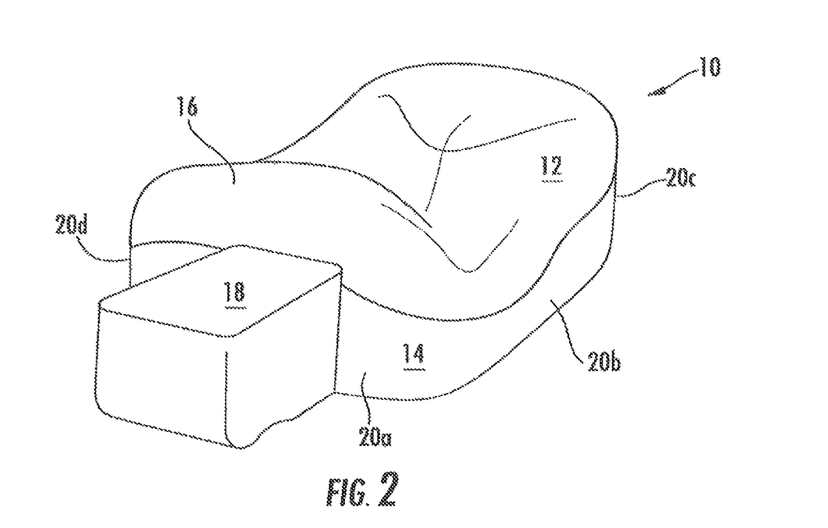
FIG. 2 is a perspective view of the embodiment of the present inventive dental restorative device shown in FIG. 1.

A first embodiment of the dental restorative device 10 in accordance with the present invention is shown in FIGS. 1 and 2. The dental restorative device 10 comprises a first layer 12 and a second layer 14 joined or fixed to the first layer 12. The first layer 12, the anatomical occlusal layer, is comprised of a dental composite material that is cured and/or heat-treated to a desired hardness and finish and is pre-formed into a first end-user configuration namely, the shape of an occlusal surface 16 replicating the anatomy of the native or natural occlusal surface of affected tooth being restored. Because the dental composite material of the first layer 12 is pre-cured the finished product will be less prone to shrinkage stress and marginal gaps that may be encountered when composite materials are cured by the dental professional in situ. Alternatively, the first layer can be of a suitable dental restorative material such as dental ceramic. The first layer 12 preferably forms only the occlusal surface 16 and lacks sidewalls that would form the buccal, lingual, distal and mesial sides of the affected tooth.

The second layer 14, the sub-layer, generally comprises an uncured dental composite and is joined to the first layer 12 by known dental techniques, including cementing or bonding. A handle 18 is integrally formed with the second layer 14 and is also composed of an uncured dental composite material. The uncured second layer has a second end-user configuration that includes a plurality of sidewalls that generally replicate the native or natural buccal, lingual, distal and mesial sides of the affected tooth. The handle 18 extends from the sidewall 20a of the second layer 14 that corresponds to the buccal side of the affected tooth. Because the second layer 14 is uncured it remains moldable "chair-side" giving the present inventive dental restorative device customizable aspects typically associated with multi-visit, costly indirect restorations.

Because the handle 18 is uncured it will be treated to have sufficient rigidity before it can be grabbed by a dental instrument, such as a cotton tweezers, during preparation and fitting of the dental restorative device 10. The portion of the second layer 14 comprising the handle 18 can also be spot cured, resulting in a handle with sufficient rigidity to be grasped by a dental instrument. Once the dental restorative device is ready for placement on the affected tooth, the handle 18, when uncured, can be removed when excess restoration material from the second layer is removed from the restoration area or can be trimmed off if it has been spot-cured.

Figure 3:
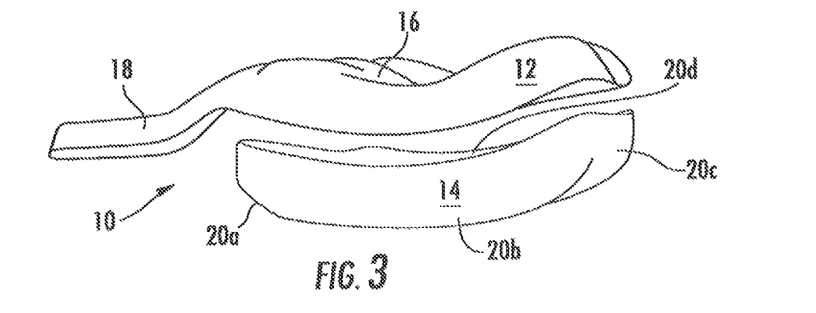
FIG. 3 is a perspective view of another embodiment of the present inventive dental restorative device.

FIG. 3 shows another embodiment of the present invention where the dental restorative device 10 comprises a first layer 12 and a second layer 14 joined or fixed to the first layer 12 and the handle 18 is integrally formed with and extending outward from the first layer 12. Similar to the embodiment shown in FIGS. 1-2, the first layer 12 is the anatomical occlusal layer and is comprised of a dental composite material that is cured and/or heat-treated to a desired hardness and finish and is pre-formed into a first end-user configuration namely, the shape of an occlusal surface 16 replicating the anatomy of the native, natural occlusal surface of the affected tooth. The second layer 14, the sub-layer, generally comprises an uncured dental composite and is joined to the first layer 12 by known dental techniques, including cementing or bonding.

FIGS. 4-12 show another aspect of inventive dental restorative device 10, namely, a packaging system 30 to support a hybrid, multi-layered dental restorative device 10 with both cured/hardened and uncured portions. The packaging system 30 comprises an outer casing 32 and inner form 34. The outer casing 32 further comprises a lid 36 and bottom 38 that, when fit together, received the inner form 34 and isolate it from exterior factors, including light and physical contamination.

Referring first to the inner form 34 (FIGS. 5, 8-9), the inner form acts as a mold and support for the dental restorative device 10 and, particularly, the uncured second layer 14 of the dental restorative device 10. Because of the mold and support function, the inner form 34 is designed and configured in various sizes and shapes to correspond to dental restorative devices in accordance with the present invention in various sizes and shapes. For embodiments of the present inventive dental restorative device 10 where the handle 18 is integrally formed with the second layer 14 the inner form 34 will also define the size, shape and location of the handle 18. The inner form 34 has an outer circumference 40 of a size and shape that generally corresponds to the size of the platform portion 42 of the bottom 38. A chamber 44 is formed into the inner form 34 to receive the dental restorative device 10. The chamber 44 includes a main section 46 and a handle section 48.

The material selection and thickness of the inner form 34 is dictated by the need for the inner form 34 to support the dental restorative device 10 before the second layer 14 is cured and hardened, maintain flexibility, facilitate ease of removal of the dental restorative device 10 from the inner chamber 44 without distorting or damaging the shape of the uncured material in the second layer 14. The inner form 34 also must act as a barrier against transmission of moisture, ambient light, or other contaminants into the inner chamber 44 while effectively facilitating thermal conductivity during preparation of the dental restorative device 10 for use in a restoration procedure, as described in greater detail below. The inner form 34 is preferably composed of an opaque or essentially opaque polypropylene thermoplastic with a thickness of 2-6 mm.

Figure 5:
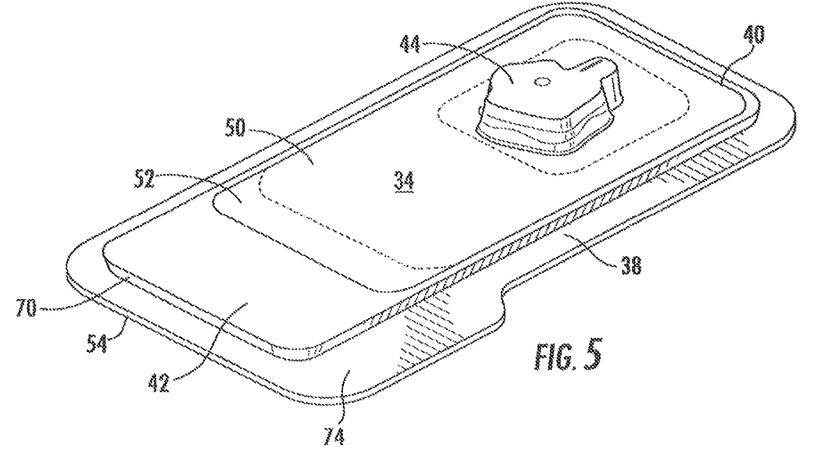
FIGS. 5-12 are perspective views of components of the packaging system of FIG. 4.
Figure 6:
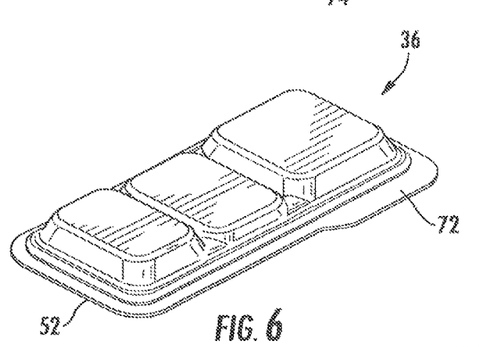
Figure 10:
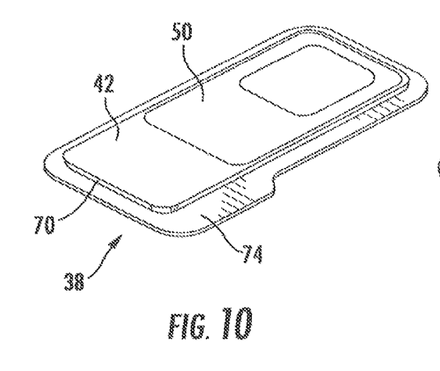
Figure 11:
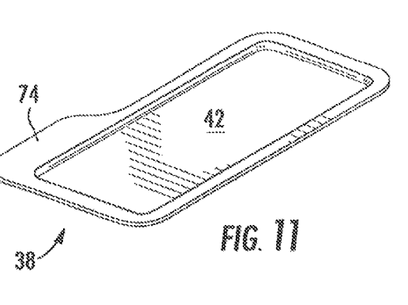
Figure 12:
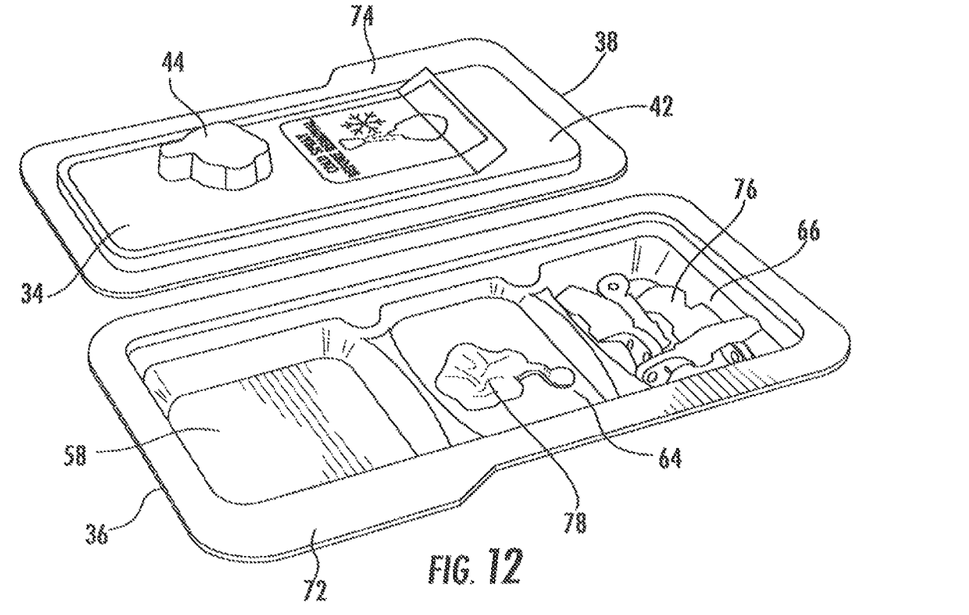

The outer casing 32 comprises the lid 36 and bottom 38. The bottom 38 is a rigid platform to support the inner form 34 and includes the platform portion 42 on which the inner form 34 sits and generally corresponds in shape and size to the outer circumference of the inner form 34. The inner form 34 may also be adhered to the bottom 38 using standard methods and protocols from the medical device industry. If the inner form 34 is adhered to the bottom 38 it is done so in a manner that allows for the easy separation and removal of the inner form 34 from the bottom 38. This can be accomplished through the use of a medical grade adhesive film 50 (FIG. 10). As seen in FIG. 5, the adhesive film 50 is less than the area of the inner form 34 enabling the un-adhered portion of the inner form 52 to act as a pull tab to separate the inner form 34 from the bottom 38.

Figure 7:
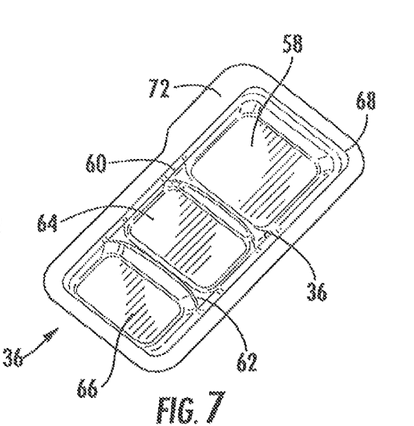
Figure 8:
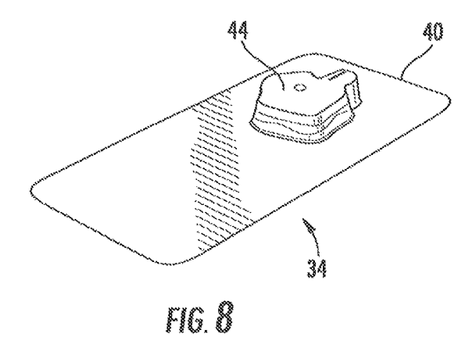
Figure 9:
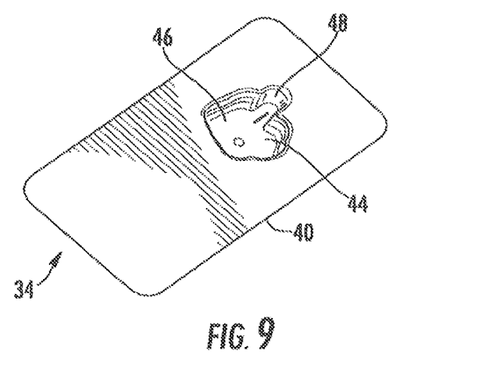

The lid 36 has an outer circumference 52 and configuration that generally corresponds with the outer circumference 54 and configuration of the bottom 38 to form a uniformly sized outer casing when the lid 36 and bottom 38 are joined together. The lid 36 includes an inner chamber 56 comprising at least a first section 58 that receives and covers the chamber 44 of the inner form 34. As seen in FIG. 7, a first and second partition 60, 62 divide the chamber 58 into a second and third section 64, 66. These auxiliary sections can hold accessory items 76, 78 (FIG. 12) used during the restoration procedure, including dental wedges and other equipment that may be useful to package with the dental restorative device 10 as part of a kit. The first and second partitions 60, 62 should extend to the platform portion 42 of the bottom 38 to keep the auxiliary sections 64, 66 separate from the first section 58 and to prevent the contents of the auxiliary sections 64, 66 from entering the first section 58. In these figures the partitions 60, 62 are formed or pressed directly into the lid 36.

Figure 4:
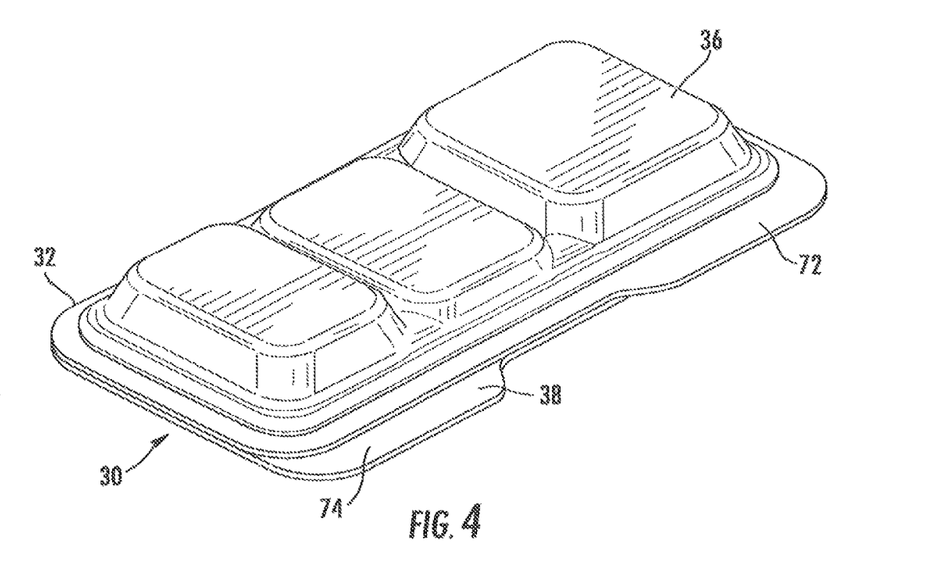
FIG. 4 is a perspective view of a packaging system for the inventive dental restorative devices of FIGS. 1-3.

The lid 36 and bottom 38 of the outer casing 32 fit tightly together to form a barrier between the inner chamber 56 of the lid 36 and the outside environment. The barrier or seal prevents or inhibits ambient light transmission into the inner chamber 56 as well as well as forming a moisture barrier and barrier against other contaminants. To form a suitable seal and barrier the lid 36 and bottom 38 fit together in an annular snap-fit arrangement with a first locking lip or ridge disposed on the periphery 68 of the ingress to the inner chamber 58 of the lid 36 and a corresponding second locking lip or ridge on the periphery 70 of the platform portion 42 of the bottom 38. In an alternative arrangement, the periphery 68 of the ingress to the inner chamber 58 and periphery 70 of the platform portion 42 may be dimensioned to press-fit or friction-fit together. A first tab 72 is formed into outer circumference of the lid 36 and second tab 74 is formed into the outer circumference of the bottom 38. The tabs 72, 74 are disposed at opposite corners of the packaging 30 to facilitate ease of separating the lid 36 from the bottom 38 during operation of the packaging system 30 (FIG. 4). The tabs 72, 74 may also be disposed at diagonal corners of the packaging system and have the same effect. The lid 36 and bottom 38 are formed of an opaque or essentially opaque material to prevent ambient light transmission into the inner chamber 58 of the lid 36 which could prematurely begin to cure the uncured second layer 14 of the dental restorative device 10.

In another aspect of the present invention an inventive dental restorative device according to FIGS. 1-3 are sold in kits with dental restorative devices for use in restoring upper or lower affected teeth. As described in detail above, the dental restorative device 10 is a hybrid ceramic dental crown made of two parts, namely, a cured anatomical occlusal layer and an uncured sub-layer with a handle on the buccal side. Kits are prepared for upper and lower molars and premolars, in various shades, including, but not limited to, shade A3 HT (High Translucency), in five different sizes. A kit for restoring upper affected teeth may include: dental wedges 76 (FIG. 12), a replica restoration 80 (FIG. 15) and a plurality of dental restorative devices in the following sizes: 15/14—XS, S, M, L, XL; 17/16—XS, S, M, L, XL; 24/25—XS, S, M, L, XL; and 26/27—XS, S, M, L, XL. The anatomy of each dental restorative device type is common to two teeth, the first and second of each tooth group. For example, a dental restorative device in size 15/14 can be used to restore a first or second upper right premolar.

Figure 15:
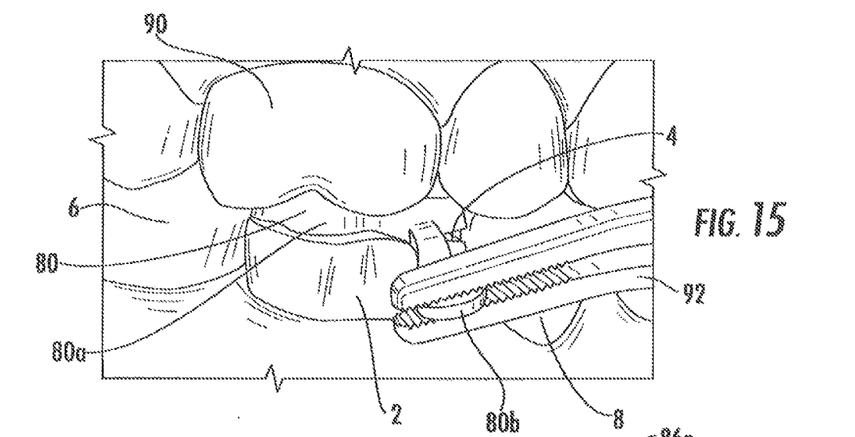
Figure 16:
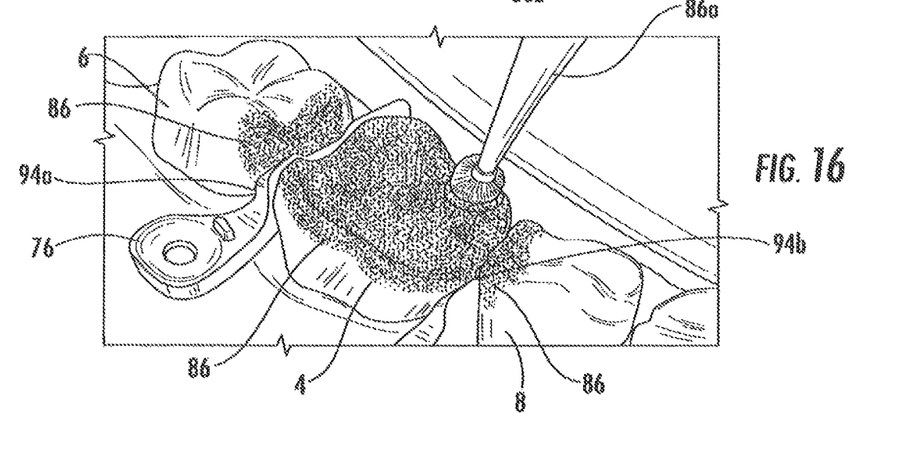

The kit may further include a corresponding number of gauges/selector keys 82 (FIG. 13) color-coded for use with upper molars or upper pre-molars. The kit may also comprise additional equipment used in the restoration procedure, including, a carving instrument 84 (FIG. 24) for removing excess uncured material, and a separating agent 86 (FIG. 16). A kit for restoring lower affected teeth would include a replica restoration 80 (FIG. 15) and a plurality of dental restorative devices in the following sizes: 34/35—XS, S, M, L, XL; 45/44—XS, S, M, L, XL; 36/37—XS, S, M, L, XL; and 47/46—XS, S, M, L, XL, in addition to the equipment noted above with the upper kit.

The replica restorations 80 are disposable silicone replicas of the cured, first layer of the dental restorative device 80*a* and a handle 80*b* matching the effected tooth 2 (FIG. 13) type and size. The replica restoration 80 is used to confirm that the occlusal clearance obtained during preparation of the effected tooth 2 is sufficient. It also provides a good visual of the overall 3D position of the dental restorative device on the restoration area 4 (FIG. 14) of the affected tooth 2 and the relationship with adjacent and opposing dentition (FIG. 15).

Figure 13:
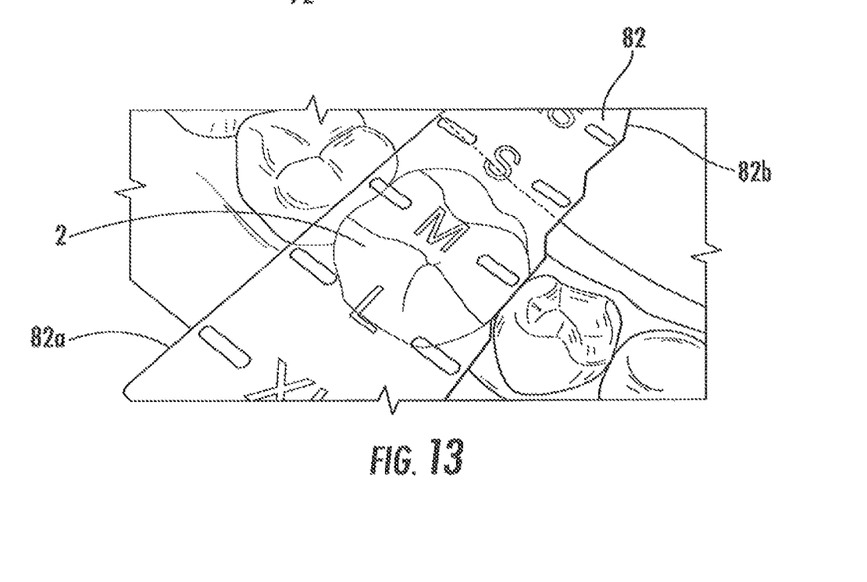
FIGS. 13-30 are perspective views of steps in the method of use of inventive dental restorative device of FIGS. 1-3 and the packaging system of FIGS. 5-12.
Figure 14:
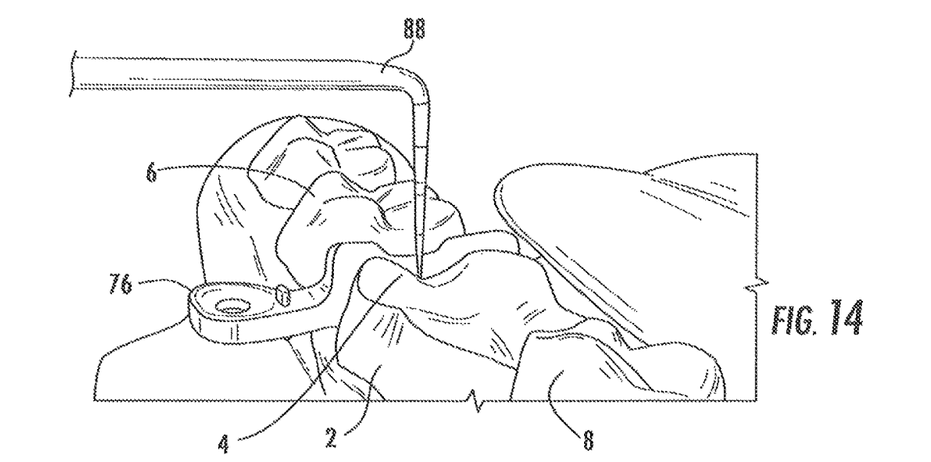
Figure 23:
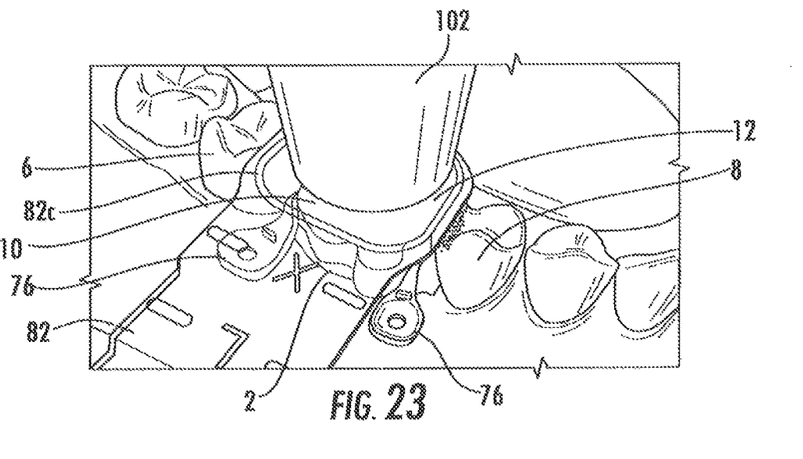

The selector keys 82 are disposable gauges made of transparent material, available in four types—upper molar (UM), lower molar (LM), upper premolar (UPM) and lower premolar (LPM). The selector keys 82 have a dual function. First, selector keys 82 are used to determine the mesial-distal (M-D) distance of the affected tooth 2 to assist in proper selection of a dental restorative device according to the present invention. As seen in FIG. 13, the selector key 82 has a first, straight edge 82*a* and a second, stepped edge 82*b* with each step corresponding to a particular Mesial-Distal size of the affected tooth 2, e.g. XS, S, M, L, XL. The transparent nature of the selector key 82 enables the affected tooth 2 to be seen through the selector key. The second function of the selector key 82 is to facilitate the spot curing (FIG. 23) of the center of the dental restorative device 10 through the bore 82*c* in the selector key.

The separating agent 86 (FIG. 16) is preferably a water soluble paint-on separator film that dries off and leaves a thin separation layer on the affected tooth 2 and the adjacent teeth 6, 8. This product is used to isolate the restoration area 4 and adjacent teeth 6, 8 to prevent unwanted bonding of the uncured, second layer 14 of the dental restorative device 10 to treated areas of the affected tooth and the adjacent dentition.

The dental restorative device of the present invention is beneficial for restoring structurally compromised posterior teeth. Preparation, fitting and application of the inventive dental restorative devices shown in FIGS. 1-3 is in accordance with the follow steps. The Mesial-Distal (M-D) distance of the affected tooth 2 being restored is determined using the selector key 82 (FIG. 13) to confirm the size of the dental restorative device 10 to repair and restore the affected tooth 2. An old restoration and/or damaged or decayed sections is then removed from the affected tooth 2 using standard dental procedures and protocols and reduces the occusal surface of the affected tooth 2 by approximately 1 mm. The preparation of the restoration area 4 may be similar to that of an overlay or occlusal top. At least 1 mm of clearance should be allowed in the central fossa and 1.5 mm at the cusps and marginal ridges. The restoration area 4 depth can be measured with a periodontal probe 88 using the adjacent dentition 6, 8 as a reference point. If portions of the restoration area 4 are deeper than 3 mm they should be built up with composite before proceeding with the restoration method. If a buildup is necessary, sufficient occlusal clearance should be left and corrections should be made after checking opposing dentition.

Once the restoration site 4 has been cleared of old restoration material and/or damaged tooth material and the proper sized dental restorative device 10 is selected, the next step is the replica restoration try-in using a disposable silicon replica restoration 80 of the inventive dental restorative device 10. The replica restoration 80 is used to confirm that the occlusal clearance obtained during preparation of the restoration site 4 of the affected tooth 2 is sufficient and provides a good visual of the overall position of the dental restoration and relationship with the adjacent 6, 8 and opposing dentition 90. The replica restoration 80 is gripped by its handle 80*b* with a tweezers 92 or forceps and placed on the restoration site 4 of the affected tooth 2 to confirm the mesial/distal fit. The patient bites down with the replica restoration 80 in place to ensure there is adequate occlusal clearance. The replica restoration 80 should have sufficient space to move when the handle 80*b* is gently tugged by the tweezers 92.

As shown in FIG. 16, once the restoration area 4 is confirmed to be of proper dimension, the restoration area is further prepared with suitable dental wedges 76 to separate the affected tooth 2 from the adjacent teeth 6, 8 and to expand the interproximal space 94*a*, 94*b* between these teeth 2, 6, 8. The dental wedges 76 also block out undercuts and expose contact points between the affected tooth 2 and adjacent teeth 6, 8. Suitable dental wedges 76 are the dental wedges disclosed and described in International Appl. No. PCT/US2013/043733 to Rhondium Limited entitled Dental Wedge with Asymmetric Sides. An applicator 86*a* is used to apply the separating agent 86 is applied to restoration area 4 of the affected tooth 2 and the adjacent teeth 6, 8 to prevent the uncured material in the dental restorative device 10 from prematurely bonding to these teeth.

Figure 17:
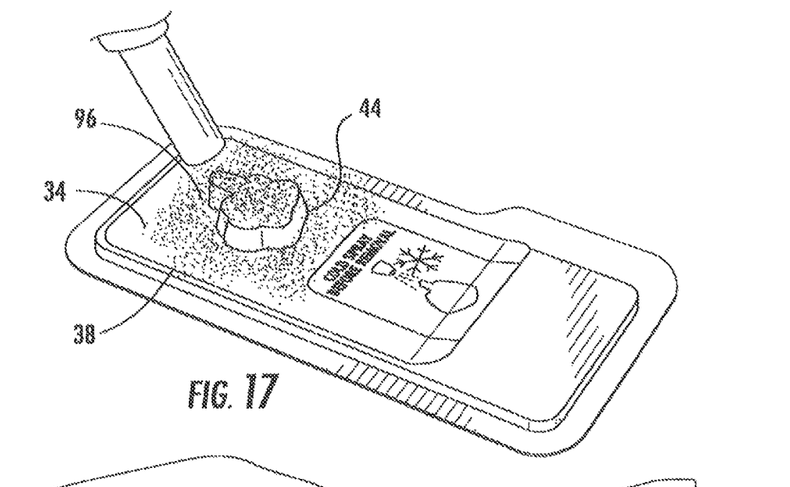
Figure 18:
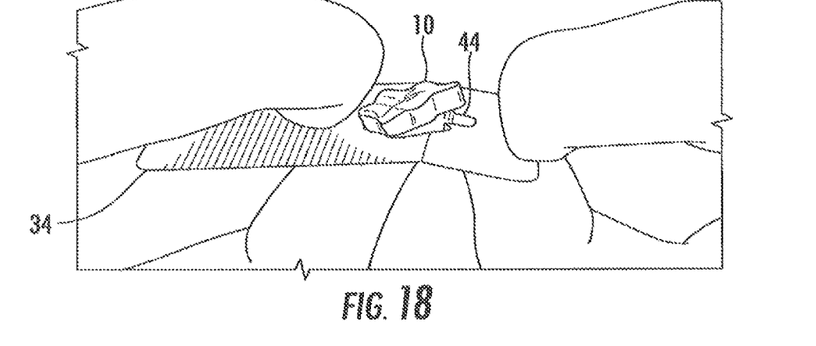
Figure 19:
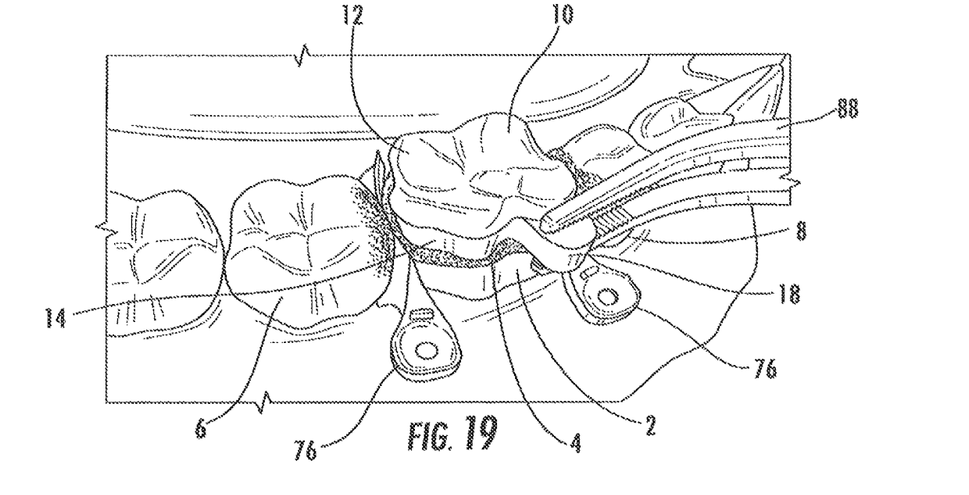

In the next step (FIG. 17), the preselected dental restorative device 10 is removed from the inner form 34. The preferred clinical method includes cooling the uncured composite resin of the second layer 14 to below 0° C. (−32° F.). Ideally the temperature should be lower than −18° C. ($\cong$−1° F.). The inner form 34 is sprayed with an endodontic chilling spray 96 to achieve the desired temperature. Cooling the uncured composite resin to a below zero temperature in a refrigerator is also acceptable. The purpose of the cooling is to increase the viscosity of the uncured composite so that it is much easier to manage and to temporarily harden the handle 18 when it is made from uncured composite material. As shown in FIGS. 18-19, once the uncured portions of the dental restorative device 10 are temporarily hardened through the cooling procedure, the dental restorative device can be easily pushed from the chamber 44 of the inner form 34 and gripped at the handle 18 with a dental instrument 92, such as a tweezers or forceps. As seen in FIG. 18, the flexible film comprising the chamber 44 of the inner form 34 can be pushed inside-out causing the cold, hardened dental restorative device 10 to pop out from the chamber 44. It is also contemplated that flexible film comprising the chamber 44 of the inner form 34 would also enable use of a dental instrument to pull the dental restorative device 10 from the chamber 44.

A typical endodontic cooling spray will keep the uncured composite resin hardened for approximately 15 seconds. The cooling step also allows for the dental restorative device 10 to be transported from its package directly into the patient's mouth. The packaging system 30, and specifically the inner form 34, is designed for the direct transport of the dental restorative device 10 into the patient's mouth, decreasing potential contamination of the device.

Figure 20:
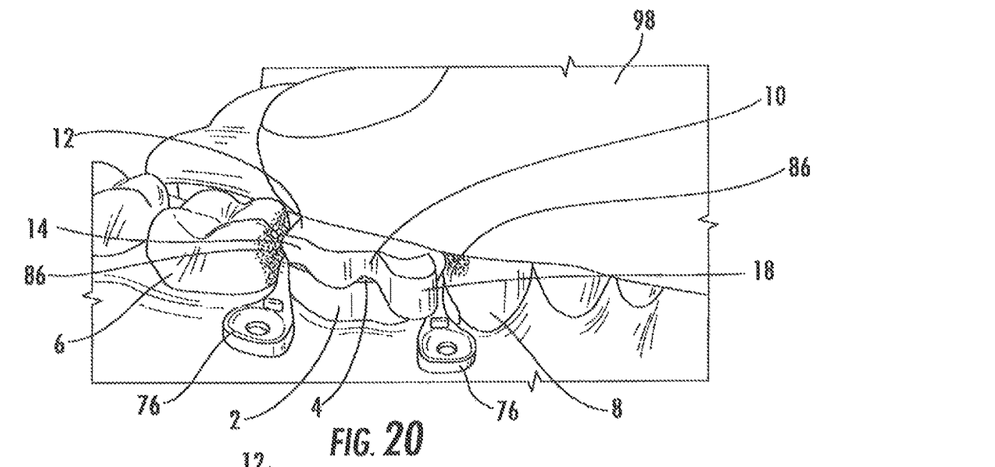
Figure 21:
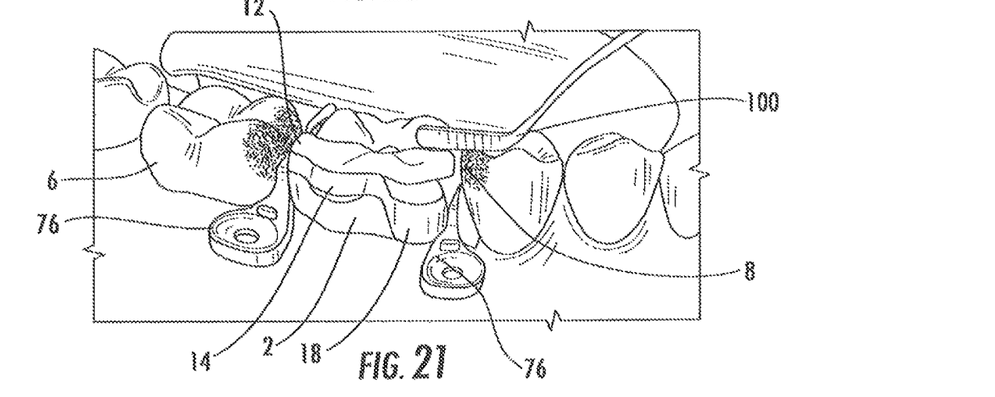
Figure 22:
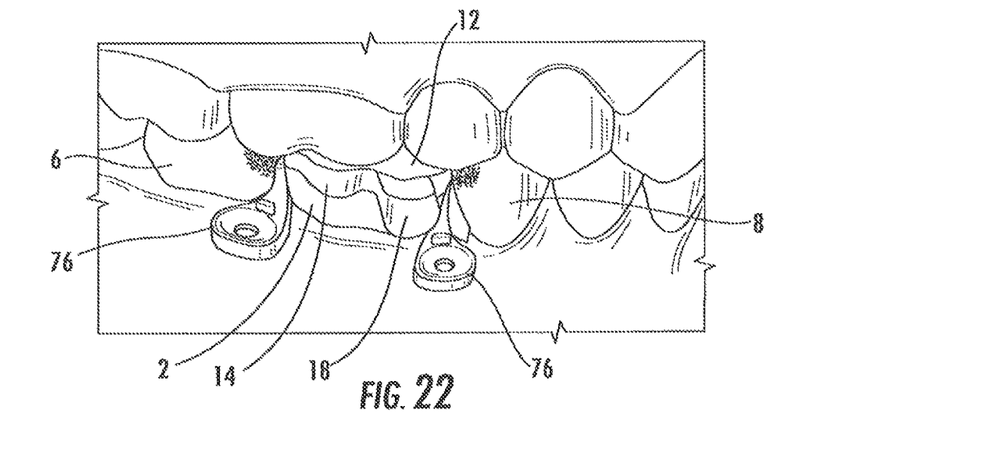

The cold, hardened dental restorative device 10 is then placed on the affected tooth 2 at the restoration area 4 (FIG. 19) and as the uncured, second layer 14 of the dental restorative device warms and softens, the device is depressed into the restoration area 4 and aligned with the adjacent teeth 6, 8 (FIG. 20). The dental restorative device 10 can be pressed into position by a finger 98. A sturdy spatula or flat plastic instrument 100 (FIG. 21) may be used to align the dental restorative device 10 with the adjacent teeth 6, 8. The patient may then bite down to confirm proper seating, vertical position and buccal/lingual alignment of the dental restorative device with the remaining tooth structure of the affected tooth 2 and the adjacent teeth 6, 8 (FIG. 22).

Figure 24:
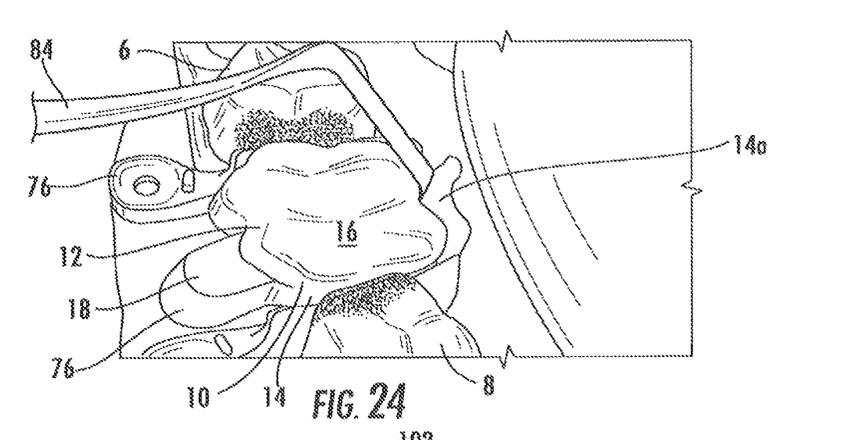

With the aid of the selector key 82 the dental restorative device 10 is spot-cured with a dental curing light 102 to cure the most light-sensitive composite material. The selector key bore 82c is aligned over the dental restorative device 10 to direct the curing light to the desired composite material. Spot-curing stabilizes the dental restorative device 10 and also decreases the movement of the dental restorative device in the patient's mouth while excess composite 14a is removed and natural contours are formed into the remaining material of the second layer 14 using a carving instrument 84 (FIG. 24).

Figure 25:
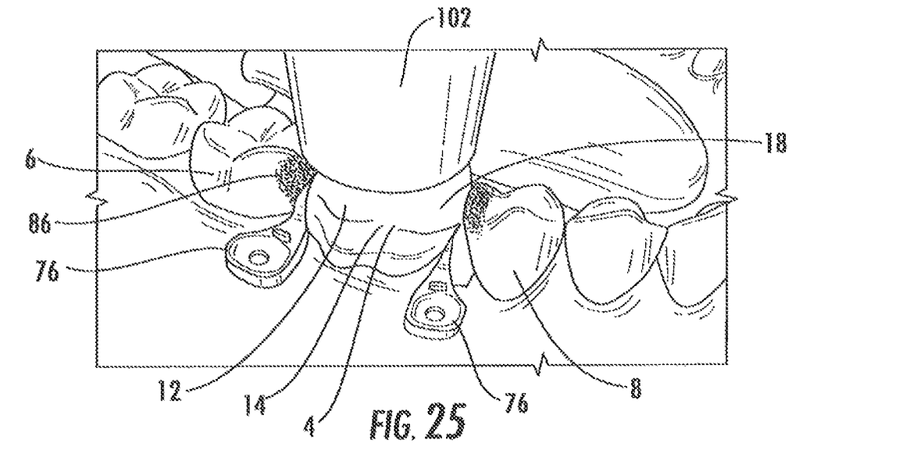
Figure 26:
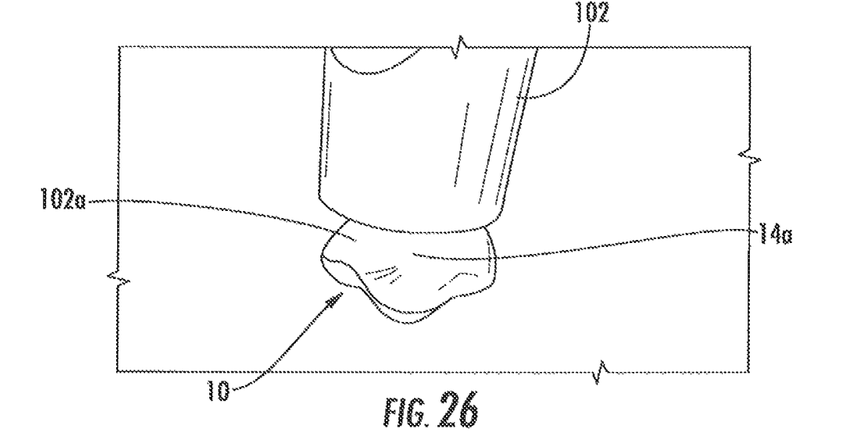

Once the excess composite material is removed, the second layer 14 of the dental restorative device 10 is completely cured with the curing light 102 (FIG. 25) and then removed from the restoration site 4 with a forceps or curved haemostat tweezers. Typically light 102a from the curing light 102 is administered to the occlusal surface and buccal and lingual side surfaces for approximately 20 second per surface/side. The underside 14a of the second layer 14 may not be fully cured and should be fully cured with light energy 102a from the curing light 102 before proceeding (FIG. 26).

Figure 27:
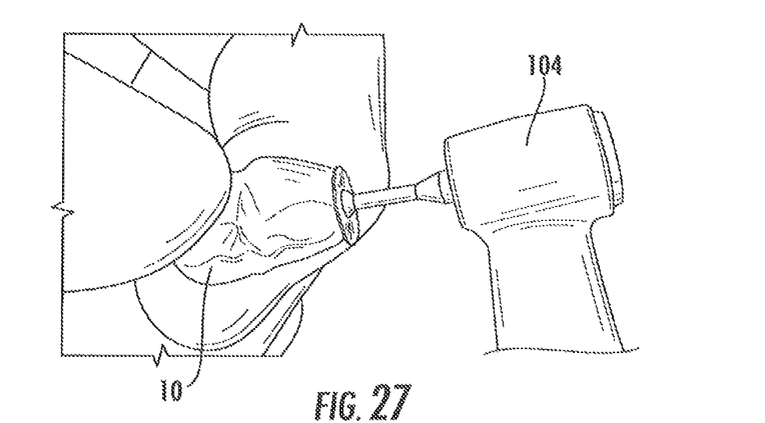
Figure 28:
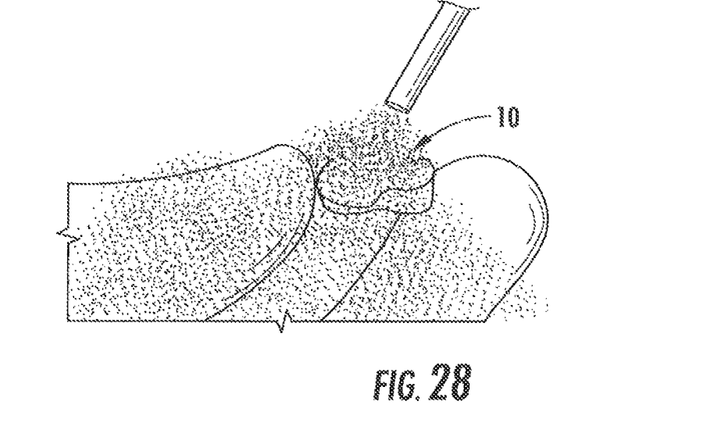
Figure 29:
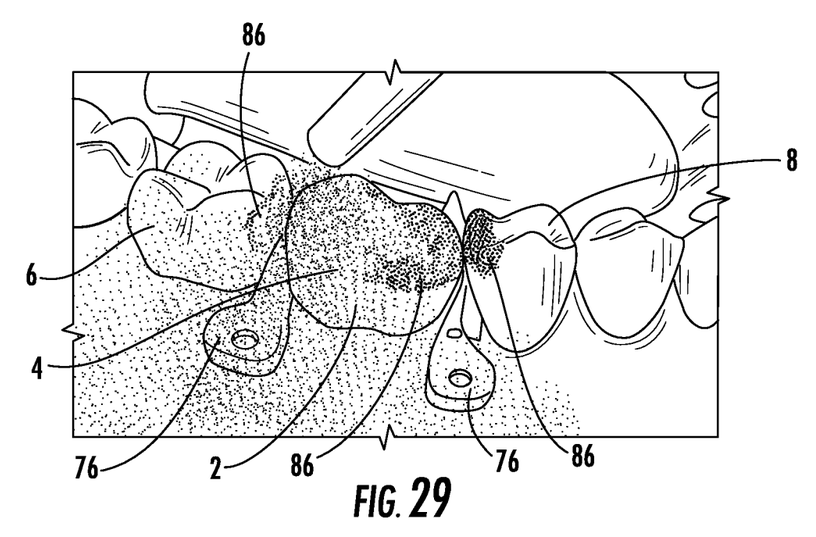
Figure 30:
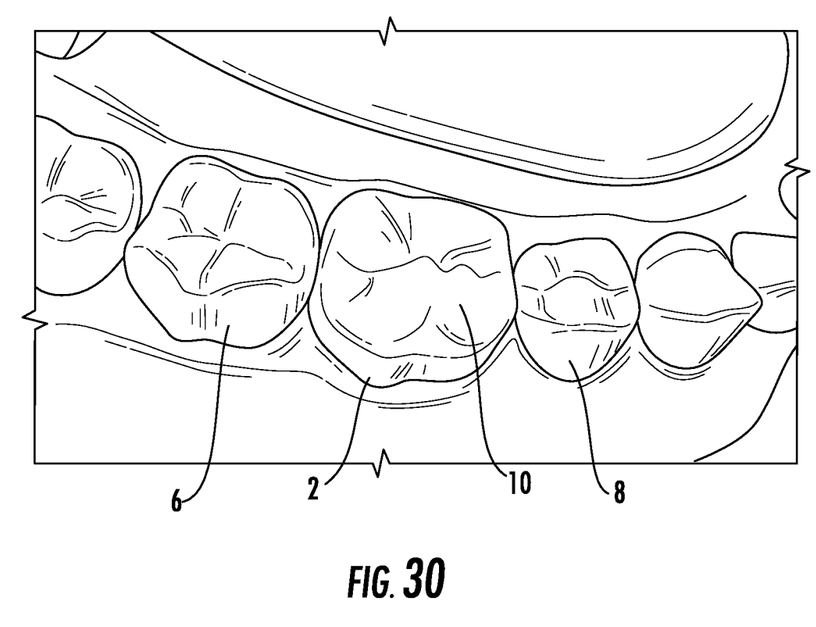

The fully cured dental restorative device 10 is then trimmed and polished as required with a suitable dental instrument 104 (FIG. 27), including trimming the handle from the dental restorative device if it is spot-cured and hardened or integrally formed with the first layer. The dental restorative device 10, restoration area 4 of the affected tooth 2 and adjacent teeth 6, 8 are cleaned and dried to ensure the separating agent 86 is removed (FIGS. 28-29). The fully cured dental restorative device 10 can then be bonded or cemented into place at the restoration site 4 of the affected tooth 2 (FIG. 30). Preferably a dual cure resin cement >30 MPA is used to bond the fully cured dental restorative device to the restoration area of the affected tooth.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

We claim:

1. A dental restorative device for use in a restoration of an affected tooth requiring restoration from a damaged state to a restored state replicating a natural, undamaged tooth, the dental restorative device comprising:
   a) a first layer composed of a first dental restoration material and formed into a first end-use configuration; and
   b) a second layer cemented or bonded to the first layer and composed of a first uncured dental composite material in a second end-use configuration forming a plurality of sidewalls replicating a buccal, lingual, mesial and distal sidewall of the natural, undamaged tooth, wherein each of the plurality of sidewalls in the second layer extends gingivally of the first layer.

2. The dental restorative device of claim 1 wherein the first dental restoration material composing the first layer is a cured dental composite material.

3. The dental restorative device of claim 1 wherein the first dental restoration material composing the first layer is a hardened dental ceramic.

4. The dental restorative device of claim 1 wherein the first end-use configuration of the first layer replicates an occlusal surface of the natural, undamaged tooth.

5. The dental restorative device of claim 1 wherein the first layer is a cured anatomical occlusal layer.

6. The dental restorative device of claim 1 wherein the first layer is a heat-treated anatomical occlusal layer.

7. The dental restorative device of claim 1 wherein the second layer is a user configurable, uncured sub-layer enabling in situ customization of the dental restorative device.

8. The dental restorative device of claim 1 further comprising a handle integrally formed with the second layer.

9. The dental restorative device of claim 1 further comprising a handle integrally formed with the first layer.

10. The dental restorative device of claim 1 wherein the first end-use configuration of the first layer forms a plurality of sidewalls replicating a buccal, lingual, mesial and distal sidewall of the natural, undamaged tooth and the plurality of sidewalls in the first layer align with corresponding sidewalls in the second layer.

* * * * *